United States Patent [19]

Hergenrother et al.

[11] Patent Number: 4,622,182

[45] Date of Patent: Nov. 11, 1986

[54] 5-(4-ETHYNYLOPHENOXY)ISOPHTHALIC CHLORIDE

[75] Inventors: Paul M. Hergenrother, Yorktown; Brian J. Jensen, Newport News, both of Va.

[73] Assignee: The United States of America as represented by the Administrator of the National Aeronautics and Space Administration, Washington, D.C.

[21] Appl. No.: 760,791

[22] Filed: Jul. 31, 1985

Related U.S. Application Data

[62] Division of Ser. No. 613,139, May 23, 1984, Pat. No. 4,587,312.

[51] Int. Cl.[4] ............................................. C07C 63/72
[52] U.S. Cl. .................................................. 260/544 P
[58] Field of Search ..................................... 260/544 P

[56] References Cited

U.S. PATENT DOCUMENTS 3,935,167 1/1976 Marvel et al. ...................... 526/90

OTHER PUBLICATIONS

Ustinov, V. A. et al., *Chemical Abstracts*, vol. 98 (1983) #143,070g.

*Primary Examiner*—Natalie Trousof
*Assistant Examiner*—L. Hendriksen
*Attorney, Agent, or Firm*—Wallace J. Nelson; Howard J. Osborn; John R. Manning

[57] ABSTRACT

Sulfone-ester polymers containing pendent ethynyl groups and a direct and multi-step process for preparing same are disclosed. The multi-step process involves the conversion of a pendent bromo group to the ethynyl group while the direct route involves reacting hydroxy-terminated sulfone oligomer or polymers with a stoichiometric amount of 5-(4-ethynylphenoxy)isophthaloyl chloride. The 5-(4-ethynylphenoxy)isophthaloyl chloride and process for preparing same are also disclosed.

1 Claim, No Drawings

5-(4-ETHYNYLOPHENOXY)ISOPHTHALIC CHLORIDE

ORIGIN OF THE INVENTION

The invention described herein was made by employees of the U.S. Government and may be manufactured and used by the Government for governmental purposes without the payment of any royalties thereon or therefor.

This is a division of application Ser. No. 613,139, filed May 23, 1984, now U.S. Pat. No. 4,587,312.

BACKGROUND OF THE INVENTION

A variety of polysulfones and polyesters are commercially available for use in different applications such as adhesives, moldings, membranes and composite matrices. The uncrosslinked forms of these materials are sensitive to certain solvents especially when they are under load. Polysulfones are not available in crosslinked forms whereas a variety of thermosetting polyesters are available. Sulfone/ester polymers have been reported but not those containing pendent ethynyl groups. Ether-ketone-sulfone polymers containing pendent ethynyl groups have been reported (C. Samyn and C. S. Marvel, *J. Polym, Sci. Polym. Chem. Ed.* 13 (1975) 1095; and in U.S. Pat. No. 3,935,167 (Marvel et al). However, the ethynyl group was introduced into the polymer through a synthetic route (Vilsmeyer reaction-conversion of an acetyl group to a chlorocinnamalaldehyde and subsequent cleavage with base to the acetylene) which does not provide a quantitative yield. This polymer containing pendent ethynyl groups was subsequently crosslinked with a catalyst (PdCl$_2$) or through reaction with terephthalonitrile N,N'-oxide.

Commercially available high performance thermoplastics such as the polyarylene ether sulfones, sold under the tradename UDEL ® (polysulfone) by Union Carbide Corporation and Victrex ® (polyethersulfone) by Imperial Chemical Industries, are recognized as tough materials. However, these materials are sensitive to certain solvents, especially under stress, and therefore are unacceptable for use in composite structures on commercial and military aircraft where resistance to long term exposure to fluids and paint strippers and temperature cycling is an essential requirement.

The present invention is directed to an improved class of high performance polymers, novel monomers and oligomers, and the process for preparing same that incorporate all the advantageous features of the prior art while minimizing or eliminating the disadvantages featured thereof.

Accordingly, it is an object of the present invention to provide a novel class of polymers having improved solvent resistance, toughness, thermoformability and mechanical performance.

Another object of the present invention is to provide chemically modified thermoplastics that are useful in making tough adhesives, coatings, membranes and composite matrices, all having improved solvent resistance.

Another object of the present invention is a novel class of sulfone-ester polymers containing pendent ethynyl groups.

A further object of the present invention is a process for preparing sulfone-ester polymers.

Another object of the present invention is the new composition of matter 5-(4-ethynylphenoxy)isophthaloyl chloride useful in the synthesis of the sulfone-ester polymers.

An additional object of the present invention is a process of making 5-(4-ethynylphenoxy)isophthaloyl chloride.

A further object of the present invention is a novel class of sulfone-ester polymers that are thermally curable without the use of a catalyst.

BRIEF DESCRIPTION OF THE INVENTION

According to the present invention, the foregoing and additional objects are attained by synthesizing sulfone-ester polymers containing pendent ethynyl groups. Two different processes have been developed to attain these polymers will be further explained hereinafter and as as depicted in Equation I below.

EQUATION I

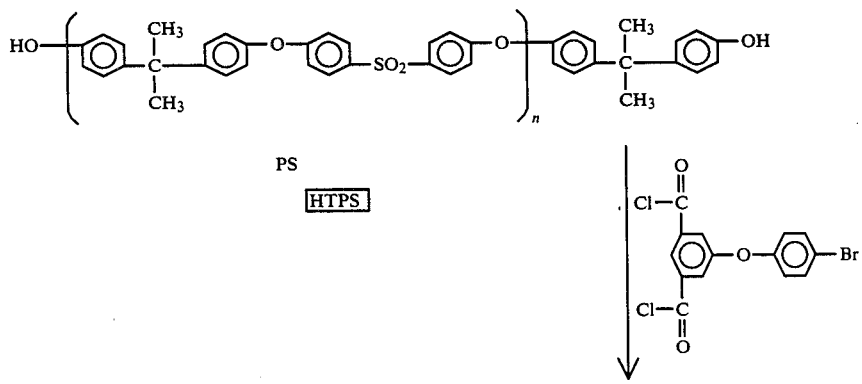

-continued
EQUATION I

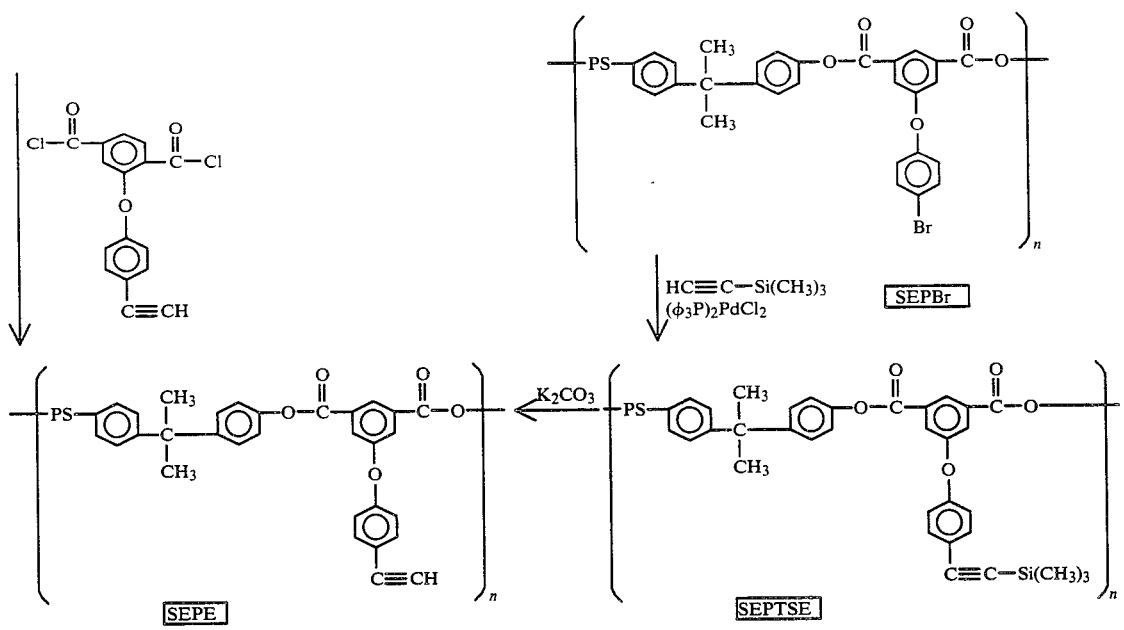

where n is an integer of 1 or greater

The preferred process or direct route is depicted in the left portion of Equation I above and involves the reaction of hydroxy-terminated sulfone oligomers, also referred to as arylene ether sulfone oligomers, with 5-(4-ethynylphenoxy)isophthaloyl chloride. The multistep route is shown in the right portion of the equation and involves the reaction of hydroxy-terminated sulfone oligomers or polymers with 5-(4-bromophenoxy)isophthaloyl chloride to form a sulfone-ester polymer containing pendent bromo groups. The bromo groups are displaced by trimethylsilylacetylene using a palladium catalyst followed by cleavage of the trimethylsilyl group to the ethynyl group with a weak base.

The ethynyl group content and accordingly, the crosslink density of the cured polymer, in both routes may be readily controlled by adjusting the molecular weight of the hydroxy terminated sulfone oligomer and by mixing other diacid dichlorides without ethynyl groups (e.g., isophthaloyl chloride, terephthaloyl chloride, 4,4'-methylenebisbenzoyl chloride, and the like) with the 5-(4-ethynylphenoxy)isophthaloyl chloride. Also, polymers having high ethynyl content can be prepared by the reaction of 5-(4-ethynylphenoxy)isophthaloyl chloride with dihydroxy compounds such as bis-phenol A, 4,4'-oxydiphenol, 4,4'-oxydithiophenol, resorcinol, hydroquinone, 4,4'-dihydroxybiphenyl, and the like. High molecular weight hydroxy terminated polymers, even up to number average molecular weights of 50,000 g/mole, can be reacted with 5-(4-ethynylphenoxy)isophthaloyl chloride and mixtures thereof with the other diacid chlorides to yield sulfone-ester polymers containing pendent ethynyl groups according to the present invention. High ethynyl group content provides high crosslink density in the cured resin. The material properties of toughness, stiffness, solvent resistance and processability are also controlled by ethynyl group content and accordingly, crosslink density. Polymers containing high ethynyl group content are generally more difficult to process (less flow due to reaction of the ethynyl groups) than those with lower ethynyl group content and when cured, are not as tough as those with with lower ethynyl group content (lower crosslink density). Conversely, cured polymers with higher ethynyl group content (higher crosslink density) are stiffer (higher modulus) and have better solvent resistance and higher use temperature.

The synthesis of sulfone-ester polymers containing pendent ethynyl groups can be readily controlled to adjust the chemical composition for use in specific applications. As prepared, the sulfone-ester polymers containing pendent ethynyl groups are readily soluble in a variety of solvents such as chloroform, m-cresol, cyclohexanone, and N,N-dimethylacetamide. Solutions can be used to cast films, form coatings, or impregnate reinforcement to form adhesive tapes and prepregs. The solvent can be removed and when the resultant polymer is heated in the 200°–300° C. range, the ethynyl groups react to provide branching and crosslinking. The cured resin is insoluble although swelling in certain solvents is observed, depending upon the crosslink density.

Having generally described the invention, a more complete understanding thereof can be obtained by reference to the following specific examples which are provided herein for purposes of illustration only and are not to be limiting on the invention.

EXAMPLES

Example I

5-(4-Bromophenoxy)isophthaloyl chloride

The synthetic route to 5-(4-bromophenoxy)isophthaloyl chloride is depicted in Equation II below. Potassium 3,5-dimethylphenoxide (1.0 mole) was reacted with 1,4-dibromobenzene (2.0 moles) in the presence of copper at 200° C. under nitrogen for two hours. The hot reaction mixture was poured into aqueous potassium hydroxide and subsequently filtered. The resulting oily filtrate was extracted with methylene chloride and the organic phase was washed with water. The methylene chloride was removed and the residue was distilled under vacuum to provide 1-(4-bromophenoxy)-3,5-dimethylbenzene as a colorless liquid in 60% yield. 1-(4-Bromophenoxy)-3,5-dimethylbenzene was oxidized with potassium permanganate (6:1 molar ratio) in a 1:1 mixture of pyridine and water at 90° C. for six hours. The brown reaction mixture was filtered and the filtrate was acidified to afford 5-(4-bromophenoxy)isophthalic acid (m.p. 310°–320° C.) in 80% crude yield. The dicarboxylic acid was refluxed in excess thionyl chloride containing a few drops of N,N-dimethylformamide for six hours. The excess thionyl chloride was removed under vacuum to yield an orange residue which was recrystallized twice from heptane to afford 5-(4-bromophenoxy)isophthaloyl chloride as pale yellow crystals, m.p. 80°–81° C.

Example II

Dimethyl-5-(4-bromophenoxy)isophthalate 5-(4-Bromophenoxy)isophthalic acid was boiled in methanol containing a catalytic amount of sulfuric acid for eighteen hours. Upon cooling, white crystals of dimethyl-5-(4-bromophenoxy)isophthalate formed in a 70% yield. Differential thermal analysis (heating rate of 5° C./min) showed two endotherms peaking at 86° and 91° C. due to two different crystal forms. Calculated for $C_{16}H_{13}BrO_3$: C, 52.63%; H, 3.59%; Br, 21.88%. Found: C, 52.43%; H, 3.67%; Br, 21.89%.

Example III

5-(4-Ethynylphenoxy)isophthaloyl Chloride

The synthetic route to the diacid chloride is also shown in Equation II. A mixture of dimethyl-5-(4-bromophenoxy)isophthalate (14.6 g, 0.040 m), dichlorobis(triphenylphosphine)palladium (0.1 g), triphenylphosphine (0.4 g), and trimethylsilylacetylene (5.5 g, 0.05 m) were stirred in triethylamine (70 ml) at approximately 80° C. for four hours under nitrogen. The cooled reaction mixture was filtered to yield a gray solid and orange filtrate. The gray solid was washed with water to provide a water-insoluble solid (4.1 g), m.p. 106°–108° C. The filtrate was concentrated to dryness to yield a tan solid (10.9 g) which melted at 82°–87° C., resolidified and remelted at 101°–105° C. The gray and tan solids were combined (15.0 g, 98% crude yield) and recrystallized from hexanes (200 ml) to afford dimethyl-5-(4-trimethylsilylethynylphenoxy)-isophthalate as light tan crystals (12.0 g) which softened at 83° C., resolidified and melted at 108°–109° C. Calculated for $C_{21}H_{22}O_5Si$: C, 65.95%; H, 5.80%; Si, 7.34%. Found: C, 66.04%; H, 5.96%; Si, 7.20%.

Powdered potassium carbonate (3.0 g) was added to a solution of dimethyl-5-(4-trimethylsilylethynylphenoxy)-isophthalate (5.0 g) in a mixture of methanol (80 ml) and dioxane (20 ml). A crystalline precipitate gradually formed upon stirring at ambient temperature for two hours. The reaction mixture was diluted with water (100 ml) and filtered to yield dimethyl-5-(4-ethynylphenoxy)isophthalate as a tan crystalline solid (3.0 g), m.p. 124°–125° C. Calculated for $C_{18}H_{14}O_5$: C, 69.67%; H, 4.55%. Found: C, 69.76%; H, 4.84%.

Dimethyl-5-(4-trimethylsilylethynylphenoxy)isophthalate and dimethyl-5-(4-ethynylphenoxy)isophthalate were saponified separately by boiling for two and one-half hours in a mixture of dioxane and aqueous sodium hydroxide. The pale yellow filtrate was acidified to yield a white solid which was recrystallized by dissolving 2.5 g in acetone (90 ml), adding hot water (90 ml) and cooling. Small white needles (2.1 g) of 5-(4-ethynylphenoxy)isophthalic acid separated which melted at 254°–256° C. dec. (introduced into preheated oil bath at 250° C.). When heated from ambient temperature, the white needles turned pale yellow at 218° C., yellow at approximately 230° C. and orange at approximately 245° C. and did not melt less than 280° C. By DTA at a heating rate of 5° C./min, no melting endotherm was visible although a strong sharp exotherm peaked at 263° C. Calculated for $C_{16}H_{10}O_5$: C, 68.09%; H, 3.57%. Found: C, 67.64%; H. 3.71%.

5-(4-Ethynylphenoxy)isophthalic acid (4.0 g) was refluxed for three hours under nitrogen in oxalyl chloride (40 ml). The orange solution was concentrated to dryness under vacuum to yield a yellow residue. The residue was extracted with warm hexanes (some insolubles), the hexanes solution treated with charcoal, and the filtrate cooled to yield 5-(4-ethynylphenoxy)isophthaloyl chloride as pale yellow crystals, m.p. 68°–69° C. The infrared and proton nuclear magnetic resonance ($^1$H nmr) spectra were consistent with the proposed structure of the ethynyl diacid chloride.

EQUATION II

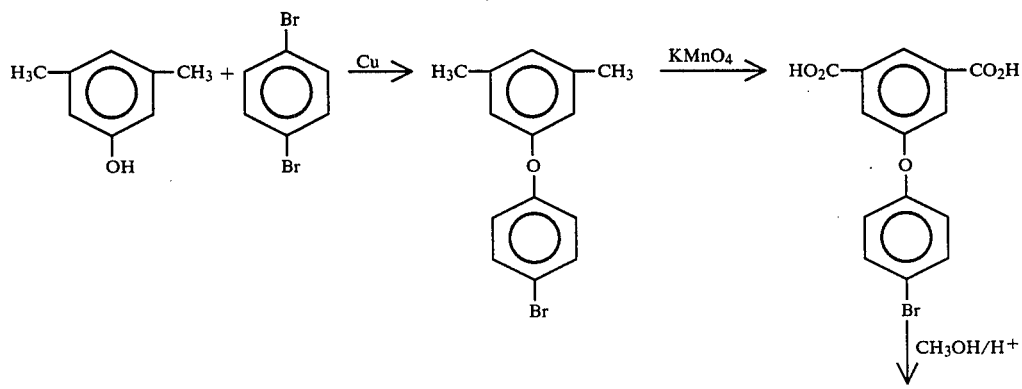

-continued
EQUATION II

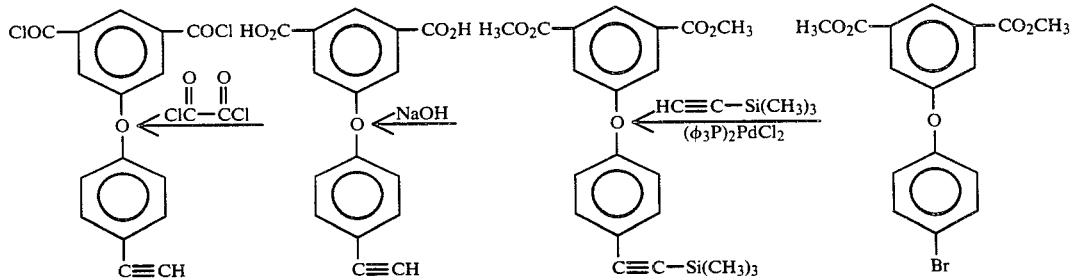

Example IV

Preparation of sulfone-ester polymer containing pendent groups using hydroxy-terminated polysulfone (HTPS) with $\overline{M}_n=2650$ Two different synthetic routes, referring back to Equation I, were used to prepare sulfone-ester polymers containing pendent groups. In the multi-step route, a stoichiometric amount (2.0677 g, 5.528 mmoles) of 5-(4-bromophenoxy)isophthaloyl chloride in dry methylene chloride (20 ml) was added dropwise to a vigorously stirred solution of HTPS ($\overline{M}_n=2650$ g/mole, 14.65 g, 5.528 mmole) in dry methylene chloride (80 ml) containing a stoichiometric excess of triethylamine (3 ml). The viscous 15% solids content reaction mixture was stirred for two hours at ambient temperature followed by quenching in methanol. The resulting white fibrous solid, sulfone-ester polymer containing pendent bromophenoxy groups (SEPBr) was thoroughly washed with methanol, dried and characterized as presented in Table I.

The sulfone-ester polymer containing pendent bromophenoxy groups (10.5 g) was dissolved in a mixture of DMAc (130 ml) and triethylamine (10 ml). Dichlorobistriphenylphosphine palladium II (0.3 g), triphenylphosphine (0.3 g) and trimethylsilylacetylene (5.0 g) were added and the reaction was stirred at 80° C. under nitrogen for four hours. The reaction mixture was poured into cold dilute hydrochloric acid to precipitate a fibrous light tan solid, trimethylsilylethynylphenoxy substituted sulfone-ester polymer (SEPTSE), which was washed successively with water and methanol. Characterization is set forth in Table I.

The trimethylsilyl group was cleaved by stirring a DMAc (130 ml) solution of the trimethylsilylethynylphenoxy substituted sulfone-ester polymer (6.0 g) with powdered potassium carbonate (4.0 g) at 25° C. for three hours and 40° C. for one hour. The polymer solution was poured into cold dilute hydrochloric acid to precipitate the sulfone-ester polymer containing pendent ethynyl groups (SEPE) as a fibrous light tan solid which was washed successively with water and methanol. Polymer characterization is presented in Table I.

By the preferred direct route, a solution of 5-(4-ethynylphenoxy)isophthaloyl chloride (0.4200, 1.316 mmole) in methylene chloride (15 ml) was added dropwise to a vigorously stirred solution of HTPS ($\overline{M}_n=2650$, 3.4876 g, 1.316 mmole) in methylene chloride (10 ml) containing triethylamine (0.319 g, 3.16 mmole) under nitrogen. The viscosity increased significantly and the reaction mixture was stirred at 26° C. for two hours. Precipitation in methanol yielded an off-white solid (SEPE) which was washed successively in water and methanol. Polymer characterization is reported in Table I.

TABLE I

| | Characterization of 2650 g/mole Hydroxy-Terminated Polysulfone Based Polymers and UDEL ® | | | | |
|---|---|---|---|---|---|
| Polymer (See Equation 1) | $\eta_{inh}{}^a$, dl/g | $GPC^b$ Peak Retention Time, Min. | $DSC^c$ $T_g$, °C. Initial | Cured$^d$ | Solubility, % Area Increase of film |
| HTPS | 0.10 | 39.73 | 152 | 152 | Soluble |
| SEPBr | 0.50 | 34.55 | 182 | 182 | Soluble |
| SEPTSE | 0.38 | 34.98 | 188 | 207 | 70 |
| SEPE | 0.34 | 37.33 | 182 | 207 | 90 |
| SEPE$^e$ | 0.64 | 33.97 | 188 | 210 | 80 |
| UDEL ® | 0.44 | 34.44 | 191 | 192 | Soluble |

$^a$Inherent viscosity, 0.5% solution in chloroform at 25° C.
$^b$Gel permation chromatography using ultra-styragel ($10^6$, $10^5$, $10^4$, $10^3$ Å), chloroform as solvent.
$^c$Differential scanning calorimetry at a heating rate of 20° C./min.
$^d$0.5 Hour at 300° C.
$^e$Made by direct route.

Example V

Preparation of sulfone-ester polymer containing pendent groups using hydroxy-terminated polysulfone (HTPS) with $\overline{M}_n=8890$ The two different synthetic routes as shown in Equation I were also used to prepare these sulfone-ester polymers containing pendent groups. In the multi-step route, a stoichiometric amount of 5-(4-bromophenoxy)isophthaloyl chloride (0.5574 g, 1.490 mmole) in dry methylene chloride (20 ml) was added dropwise to a vigorously stirred solution of HTPS ($\overline{M}_n=8890$ g/mole, 13.25 g, 1.490 mmole) in dry methylene chloride (80 ml) containing a stoichiometric excess of triethylamine (2 ml). The viscous 15% solids content reaction mixture was stirred for two hours at ambient temperature followed by quenching in methanol. The resulting white fibrous solid (SEPBr) was thoroughly washed with methanol, dried and characterized as presented in Table II.

The sulfone-ester polymer containing pendent bromophenoxy groups (10.5 g) was dissolved in a mixture of DMAc (125 ml) and triethylamine (10 ml). Dichlorobistriphenylphosphine palladium II (0.3 g), triphenylphosphine (0.3 g) and trimethylsilylacetylene (3.2 g) were added and the reaction stirred at 80° C. under nitrogen for four hours. The reaction mixture was poured into cold dilute hydrochloric acid to precipitate a fibrous light tan solid (SEPTSE) which was washed successively with water and methanol. Characterization is in Table II.

The trimethylsilyl group was cleaved by stirring a DMAc (100 ml) solution of the trimethylsilylethynylphenoxy substituted sulfone-ester polymer (9.0 g) with powdered potassium carbonate (4.0 g) at 25° C. for two hours and 40° C. for one hour. The polymer solution was poured into cold dilute hydrochloric acid to precipitate the sulfone-ester polymer containing pendent ethynyl groups (SEPE) as a fibrous light tan solid which was washed successively with water and methanol. Polymer characterization is presented in Table II.

By the preferred direct route, a solution of 5-(4-ethynylphenoxy)isophthaloyl chloride (0.1500 g, 0.4699 mmole) in methylene chloride (10 ml) was added dropwise to a vigorously stirred solution of HTPS ($\overline{M}_n$=8890, 4.178 g, 0.4699 mmole) in methylene chloride (15 ml) containing triethylamine (0.125 g, 1.24 mmole) under nitrogen. The viscosity increased significantly and the reaction mixture was stirred at 26° C. for two hours. Precipitation in methanol yielded an off-white solid (SEPE) which was washed successively in water and methanol. Polymer characterization is reported in Table II.

It is thus seen from the foregoing description and specific examples that the present invention concerns new composition of matter in 5-(4-ethynylphenoxy)isophthaloyl chloride and sulfone-ester polymers containing pendent ethynyl groups and a process for the preparation of the same. The test and tabulated results show that cured polymers containing pendent ethynyl groups offer improved solvent resistance and higher use temperature than comparable polymers (e.g., UDEL ®) void of ethynyl groups.

Although the specific examples are directed to 5-(4-ethynylphenoxy)isophthaloyl chloride, any diacid dichloride containing pendent ethynyl groups are considered applicable for practice of this invention within the scope of the appended claims. Also, although the disclosure is specifically directed toward sulfone-ester polymers containing pendent ethynyl groups, the 5-(4-ethynylphenoxy)isophthaloyl chloride and similar compounds can be used to place pendent ethynyl groups on a variety of other polymers. Thus, any soluble difunctional monomer, oligomer or polymer containing groups such as OH, $NH_2$, NHR, SH, etc., and capable of reacting with an acid chloride, can acquire pendent ethynyl groups according to the process described herein.

These and other variations and modifications of the present invention will be apparent to those skilled in the art in the light of the above teachings. It is therefore to be understood that, within the scope of the appended claims, the invention may be practiced other than as specifically described herein.

What is claimed as new and desired to be secured by Letters Patent of the United States is:

1. The compound 5-(4-ethynylphenoxy)isophthaloyl chloride.

* * * * *

TABLE II

| Polymer (See Equation 1) | Characterization of 8890 g/mole Hydroxy-Terminated Polysulfone Based Polymers | | | | |
|---|---|---|---|---|---|
| | $\eta$inh, dl/g | GPC Peak Retention Time, Min. | DSC $T_g$, °C. Initial | Cured | Solubility, % Area Increase of film |
| HTPS | 0.25 | 36.33 | 182 | 182 | Soluble |
| SEPBr | 0.84 | 32.18 | 194 | 194 | Soluble |
| SEPTSE | 0.69 | 32.84 | 195 | 197 | 110 |
| SEPE | 0.61 | 33.34 | 194 | 199 | 200 |
| SEPE[a] | 1.16 | 32.23 | 187 | 200 | 170 |

[a]Made by direct route.

UNITED STATES PATENT AND TRADEMARK OFFICE
CERTIFICATE OF CORRECTION

PATENT NO. : 4,622,182

DATED : November 11, 1986

INVENTOR(S) : Paul M. Hergenrother et al.

It is certified that error appears in the above-identified patent and that said Letters Patent is hereby corrected as shown below:

Title of invention should read:

-- 5-(4-ETHYNYLPHENOXY)ISOPHTHALIC CHLORIDE --.

Column 3, portion of the compound reading

" "
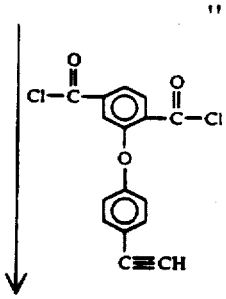      should read    -- 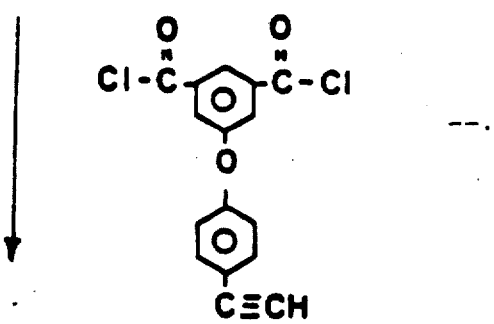 --.

Signed and Sealed this

Thirty-first Day of March, 1987

Attest:

DONALD J. QUIGG

Attesting Officer            Commissioner of Patents and Trademarks